(12) United States Patent
McCabe et al.

(10) Patent No.: US 8,007,484 B2
(45) Date of Patent: Aug. 30, 2011

(54) PANTS TYPE PRODUCT AND METHOD OF MAKING THE SAME

(75) Inventors: John A. McCabe, Sheboygan Falls, WI (US); Robert E. Andrews, Sheboygan, WI (US); James H. Rhines, Kiel, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 11/096,588

(22) Filed: Apr. 1, 2005

(65) Prior Publication Data

US 2006/0224137 A1    Oct. 5, 2006

(51) Int. Cl.
*A61F 13/15* (2006.01)
*A61F 13/20* (2006.01)

(52) U.S. Cl. ............ 604/385.27; 604/385.25; 156/166

(58) Field of Classification Search ............ 604/385.22, 604/385.24, 385.25, 385.27; 156/160, 166, 156/176, 163, 164

See application file for complete search history.

(56) References Cited

U.S. PATENT DOCUMENTS

| | | | |
|---|---|---|---|
| 135,145 A | 1/1873 | Murphy |
| 293,353 A | 2/1884 | Purvis |
| 312,257 A | 2/1885 | Cotton et al. |
| 410,123 A | 8/1889 | Stilwell |
| 432,742 A | 7/1890 | Stanley |
| 643,821 A | 2/1900 | Howlett |
| 1,393,524 A | 10/1921 | Grupe |
| 1,605,842 A | 11/1926 | Jones |
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |
| 2,164,408 A | 7/1939 | Joa |
| 2,167,179 A | 7/1939 | Joa |
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |

(Continued)

FOREIGN PATENT DOCUMENTS

BE    1007854    11/1995

(Continued)

OTHER PUBLICATIONS

Reciprocating Mechanisms, Ingenious Mechanisms for Designers and Inventors, Franklin Jones vol. 1.

(Continued)

*Primary Examiner* — Melanie J Hand
(74) *Attorney, Agent, or Firm* — Ryan Kromholz & Manion, S.C.

(57) ABSTRACT

A pants type disposable undergarment is provided which is equipped with an elasticized side panel. The side panel is elasticized with elastic film. The elastic film is attached to a nonwoven layer. The elasticized nonwoven layer is then split into two sections. A portion of the elasticized nonwoven layer is then ultrasonically cut to the desired configuration. The elastic film does not traverse the crotch region. Also provided are methods for producing such disposable undergarments.

8 Claims, 5 Drawing Sheets

U.S. PATENT DOCUMENTS

| | | |
|---|---|---|
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr. |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,913,862 A | 11/1959 | Sabee |
| 2,939,461 A | 6/1960 | Joa |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,772,120 A | 11/1973 | Radzins |
| 3,796,360 A | 3/1974 | Alexeff |
| 3,816,210 A | 6/1974 | Aoko et al. |
| 3,854,917 A | 12/1974 | McKinney et al. |
| 3,883,389 A | 5/1975 | Schott, Jr. |
| 3,888,400 A | 6/1975 | Wiig |
| 3,904,147 A | 9/1975 | Taitel et al. |
| 3,918,698 A | 11/1975 | Coast |
| 3,960,646 A | 6/1976 | Wiedamann |
| 3,991,994 A | 11/1976 | Farish |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A * | 5/1987 | Wisneski et al. ............ 428/221 |
| 4,672,705 A | 6/1987 | Bors et al. |
| 4,693,056 A | 9/1987 | Raszewski |
| 4,701,239 A | 10/1987 | Craig |
| 4,726,874 A | 2/1988 | VanVliet |
| 4,726,876 A | 2/1988 | Tomsovic et al. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,510 A | 1/1989 | Wittrock et al. |
| 4,801,345 A | 1/1989 | Dussaud et al. |
| 4,802,570 A | 2/1989 | Hirsch et al. |
| 4,840,609 A | 6/1989 | Jones et al. |
| 4,845,964 A | 7/1989 | Bors et al. |
| 4,864,802 A | 9/1989 | D'Angelo |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |

| | | |
|---|---|---|
| 4,908,175 A | 3/1990 | Angstadt |
| 4,909,019 A | 3/1990 | Delacretaz et al. |
| 4,925,520 A | 5/1990 | Beaudoin et al. |
| 4,927,322 A | 5/1990 | Schweizer et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,045,039 A | 9/1991 | Bay |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,195,684 A | 3/1993 | Radzins |
| 5,203,043 A | 4/1993 | Riedel |
| 5,213,645 A | 5/1993 | Nomura et al. |
| 5,223,069 A | 6/1993 | Tokuno et al. |
| 5,226,992 A * | 7/1993 | Morman ............... 156/62.4 |
| 5,246,433 A | 9/1993 | Hasse et al. |
| 5,267,933 A | 12/1993 | Precoma |
| 5,308,345 A | 5/1994 | Herrin |
| 5,328,438 A | 7/1994 | Crowley |
| 5,340,424 A | 8/1994 | Matsushita |
| 5,368,893 A | 11/1994 | Sommer et al. |
| 5,407,513 A | 4/1995 | Hayden et al. |
| 5,415,649 A | 5/1995 | Watanabe et al. |
| 5,421,924 A | 6/1995 | Ziegelhoffer et al. |
| 5,424,025 A | 6/1995 | Hanschen et al. |
| 5,435,802 A | 7/1995 | Kober |
| 5,449,353 A | 9/1995 | Watanabe et al. |
| 5,464,401 A | 11/1995 | Hasse et al. |
| 5,494,622 A | 2/1996 | Heath et al. |
| 5,540,647 A | 7/1996 | Weiermann et al. |
| 5,545,275 A | 8/1996 | Herrin et al. |
| 5,545,285 A | 8/1996 | Johnson |
| 5,552,013 A | 9/1996 | Ehlert et al. |
| 5,556,360 A | 9/1996 | Kober et al. |
| 5,556,504 A | 9/1996 | Rajala et al. |
| 5,560,793 A | 10/1996 | Ruscher et al. |
| 5,602,747 A | 2/1997 | Rajala |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| RE35,687 E | 12/1997 | Igaue et al. |
| 5,693,165 A | 12/1997 | Schmitz |
| 5,699,653 A | 12/1997 | Hartman et al. |
| 5,707,470 A | 1/1998 | Rajala et al. |
| 5,711,832 A | 1/1998 | Glaug et al. |
| 5,725,518 A | 3/1998 | Coates |
| 5,745,922 A | 5/1998 | Rajala et al. |
| 5,746,869 A | 5/1998 | Hayden et al. |
| 5,749,989 A | 5/1998 | Linman et al. |
| 5,788,797 A | 8/1998 | Herrin et al. |
| 5,817,199 A | 10/1998 | Brennecke et al. |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,500 A | 3/1999 | Herrin et al. |
| 5,902,431 A | 5/1999 | Wilkinson |
| 5,932,039 A | 8/1999 | Popp et al. |
| 5,938,193 A | 8/1999 | Bluemle et al. |
| 5,964,970 A | 10/1999 | Woolwine et al. |
| 6,036,805 A * | 3/2000 | McNichols ............... 156/227 |
| 6,043,836 A | 3/2000 | Kerr et al. |
| 6,050,517 A | 4/2000 | Dobrescu et al. |
| 6,074,110 A | 6/2000 | Verlinden et al. |
| 6,098,249 A | 8/2000 | Toney et al. |
| 6,123,792 A | 9/2000 | Samida et al. |
| 6,183,576 B1 | 2/2001 | Couillard et al. |
| 6,210,386 B1 | 4/2001 | Inoue |
| 6,212,859 B1 | 4/2001 | Bielik, Jr. et al. |
| 6,250,048 B1 | 6/2001 | Linkiewicz |
| 6,262,331 B1 * | 7/2001 | Nakahata et al. ............. 604/383 |
| 6,264,784 B1 | 7/2001 | Menard et al. |
| 6,276,421 B1 | 8/2001 | Valenti et al. |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,336,921 B1 | 1/2002 | Kato et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Gloug et al. |
| 6,482,278 B1 | 11/2002 | McCabe et al. |
| 6,494,244 B2 | 12/2002 | Parrish et al. |
| 6,521,320 B2 | 2/2003 | McCabe et al. |
| 6,524,423 B1 | 2/2003 | Hilt et al. |
| 6,551,228 B1 | 4/2003 | Richards |
| 6,551,430 B1 | 4/2003 | Glaug et al. |
| 6,554,815 B1 | 4/2003 | Umebayashi |
| 6,572,520 B2 | 6/2003 | Blumle |
| 6,581,517 B1 | 6/2003 | Becker et al. |
| 6,596,108 B2 | 7/2003 | McCabe |
| 6,605,172 B2 | 8/2003 | Anderson et al. |
| 6,605,173 B2 | 8/2003 | Glaug et al. |
| 6,637,583 B1 | 10/2003 | Andersson |
| 6,648,122 B1 | 11/2003 | Hirsch et al. |
| 6,649,010 B2 | 11/2003 | Parrish et al. |
| 6,659,150 B1 | 12/2003 | Perkins et al. |
| 6,659,991 B2 | 12/2003 | Suekane |
| 6,675,552 B2 | 1/2004 | Kunz et al. |
| D497,991 S | 11/2004 | Otsubo et al. |
| 6,820,671 B2 | 11/2004 | Calvert |
| 6,837,840 B2 | 1/2005 | Yonekawa et al. |
| 6,840,616 B2 | 1/2005 | Summers |
| 6,875,202 B2 | 4/2005 | Kumasaka et al. |
| 7,077,393 B2 | 7/2006 | Ishida |
| 7,172,666 B2 | 2/2007 | Groves et al. |
| 7,214,174 B2 | 5/2007 | Allen et al. |
| 7,247,219 B2 | 7/2007 | O'Dowd |
| 2001/0012813 A1 | 8/2001 | Bluemle |
| 2001/0017181 A1 | 8/2001 | Otruba et al. |
| 2002/0046802 A1 | 4/2002 | Tachibana et al. |
| 2002/0059013 A1 | 5/2002 | Rajala et al. |
| 2003/0000620 A1 | 1/2003 | Herrin et al. |
| 2003/0015209 A1 | 1/2003 | Gingrass et al. |
| 2003/0052148 A1 | 3/2003 | Rajala et al. |
| 2003/0066585 A1 | 4/2003 | McCabe |
| 2003/0083638 A1 | 5/2003 | Malee |
| 2003/0084984 A1 | 5/2003 | Glaug et al. |
| 2003/0089447 A1 | 5/2003 | Molee et al. |
| 2003/0135189 A1 | 7/2003 | Umebayashi |
| 2004/0016500 A1 | 1/2004 | Tachibana et al. |
| 2004/0108054 A1 | 6/2004 | Otsubo et al. |
| 2004/0164482 A1 | 8/2004 | Edinger |

| Pub. No. | Date | Inventor |
|---|---|---|
| 2005/0000628 A1 | 1/2005 | Norrby |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0021300 A1 | 2/2006 | Tada et al. |
| 2006/0137298 A1 | 6/2006 | Oshita et al. |
| 2006/0224137 A1 | 10/2006 | McCabe et al. |
| 2006/0265867 A1 | 11/2006 | Schaap |
| 2007/0074953 A1 | 4/2007 | McCabe |

FOREIGN PATENT DOCUMENTS

| | | |
|---|---|---|
| CA | 1146129 | 5/1983 |
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 1/2006 |
| CA | 2559517 | 5/2007 |
| DE | 102006047280 | 4/2007 |
| EP | 0044206 | 1/1982 |
| EP | 0048011 | 3/1982 |
| EP | 0089106 | 9/1983 |
| EP | 0304140 | 8/1987 |
| EP | 0439897 | 2/1990 |
| EP | 0455231 | 11/1991 |
| EP | 510251 | 10/1992 |
| EP | 0652175 | 5/1995 |
| EP | 0811473 | 12/1997 |
| EP | 0901780 | 3/1999 |
| EP | 1132325 | 9/2001 |
| EP | 1272347 | 1/2003 |
| EP | 1552802 | 7/2005 |
| EP | 1571249 | 9/2005 |
| EP | 1619008 | 1/2006 |
| EP | 1707168 | 4/2006 |
| ES | 509706 | 11/1982 |
| ES | 520559 | 12/1983 |
| ES | 296211 | 12/1987 |
| FR | 2255961 | 7/1975 |
| FR | 0206208 | 12/1986 |
| FR | 2891811 | 4/2007 |
| GB | 191101501 | 1/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2288316 | 10/1995 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 | 7/1994 |
| JP | 10035621 | 2/1998 |
| JP | 10-277091 | 10/1998 |
| SE | 0602047 | 5/2007 |
| WO | WO 9747810 | 12/1997 |
| WO | WO9907319 | 2/1999 |
| WO | WO9913813 | 3/1999 |
| WO | WO9965437 | 12/1999 |
| WO | WO0143682 | 6/2001 |
| WO | WO0172237 | 10/2001 |
| WO | WO2005075163 | 1/2005 |

OTHER PUBLICATIONS

European Search Report; S/N 062517161.0; Aug. 13, 2010.

* cited by examiner

PANTS TYPE PRODUCT AND METHOD OF MAKING THE SAME

BACKGROUND OF THE INVENTION

The present invention related to disposable undergarments and more particularly, a pants type undergarment which is equipped with elastic film which does not traverse the crotch region, and to a method of producing such undergarments.

Disposable undergarments of the children's training pant type, or of the adult incontinence type, are generally made up of two nonwoven layers of material with elastic strands of material placed between the two nonwoven layers of material thus creating an elastic web laminate. The layers of material are continuous sheets of material that are eventually cut into individual undergarments lengths. The elastic strands may be arranged and cut so that specific areas of the undergarment are free of elastic tension or forces.

Many patents describe methods of putting elastic in the leg hole area of a undergarment. For example, U.S. Pat. Nos. 5,745,922, 5,188,627, 5,660,657, 5,643,396, 5,634,917 and 5,660,657. Still, the problem remains of efficiently and securely placing elastic in other areas of the undergarment besides the leg hole areas. Securing elastic strands around the back and front waists, for example, in a secure and systematic manner is also an element of disposable undergarment design that has not been perfectly addressed in the prior art.

SUMMARY OF THE INVENTION

It is a principal object of this invention to provide an improved method of producing a pants type undergarment and to provide the resultant improved undergarment. As compared to previous designs and processes, the present invention results in less material use, a better visual appearance of the final product, and a more reliable process.

In accordance with this invention, elastic film is stretched, relaxed, and then restretched before being applied to a section of nonwoven fabric material. The elastic film section is then split into two sections and each section is cut before being applied to the undergarment chassis. The undergarment chassis is formed by splitting an indicator patch into two sections and applying the indicator patch section to a nonwoven fabric material.

In accordance with another aspect of the invention, once the elastic film sections are attached to the undergarment chassis an absorbent insert is also attached to the undergarment chassis. The absorbent insert is retained on the undergarment chassis by either folding the undergarment chassis material edges over or adhesively applying an additional layer of nonwoven material to the undergarment chassis.

In a first embodiment of the invention, the elastic film sections are cut in such a manner that additional waistband elastic is used, but leg hole elastic is not used. The method of this embodiment includes the additional step of adding waistband elastic to the undergarment chassis.

A second embodiment of the invention involves a similar method, but differs in that the elastic film is cut in a different configuration. In this embodiment the step of including leg elastic is added method described above.

A third embodiment of the invention is similar to the first embodiment, but differs in that the elastic film is cut in a different configuration. In the embodiment the step of adding a waistband elastic is eliminated.

BRIEF DESCRIPTION OF THE DRAWINGS

FIG. 2a is a top planar view of an undergarment produced according to the first embodiment of the present invention.

FIG. 2b is a top planar view of a side panel assembly of embodiment shown in FIG. 2a.

FIG. 3a is a top planar view of an undergarment produced according to the second embodiment of the present invention.

FIG. 3b is a top planar view of a side panel assembly of embodiment shown in FIG. 3a.

FIG. 4b is a top planar view of a side panel assembly of embodiment shown in FIG. 4a.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
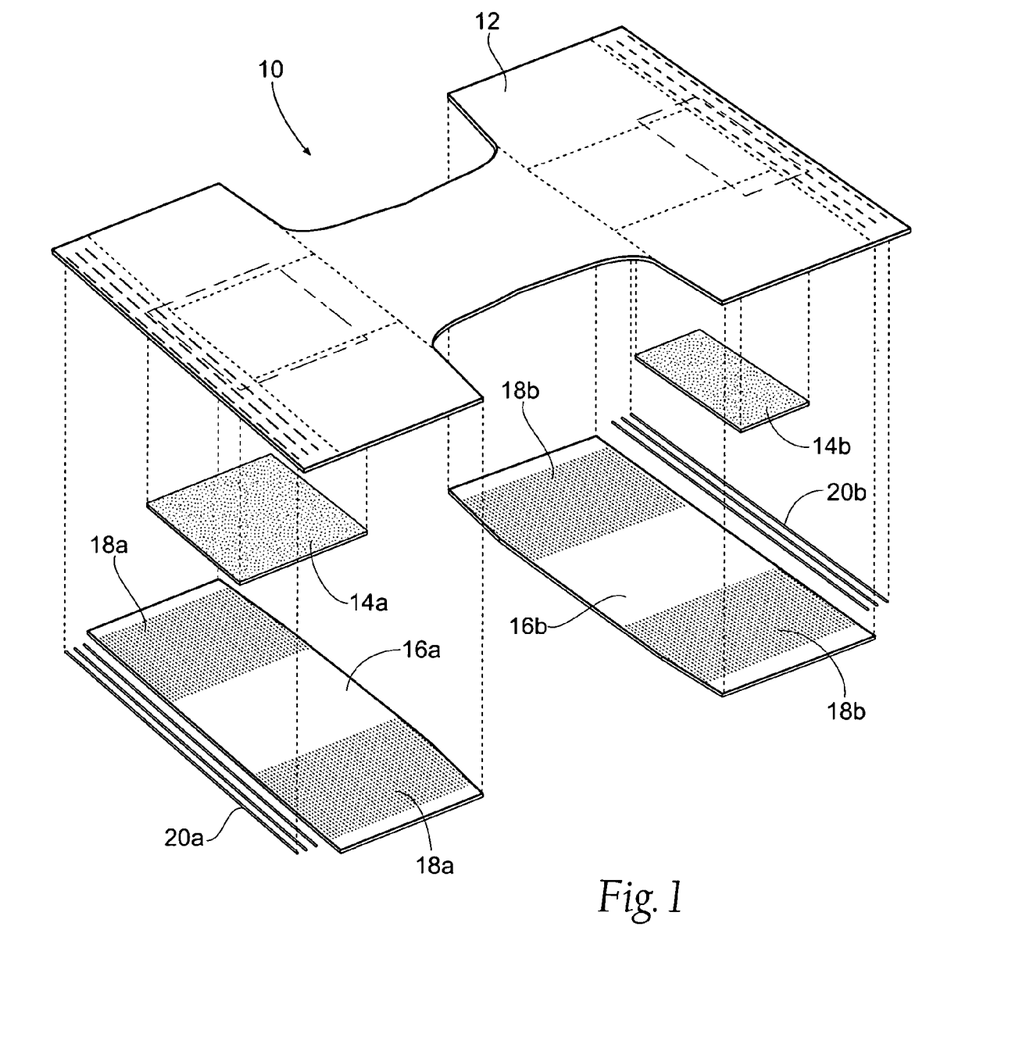
FIG. 1 is a perspective exploded view of an undergarment produced according to the present invention.

FIG. 1 shows an exploded perspective view of an undergarment 10 produced according to the present invention. The undergarment 10 includes a chassis 12, indicator patch sections 14, side panels 16 including stretch elastic film sections 18, and waistband elastic 20.

Figures 2A, 2B:
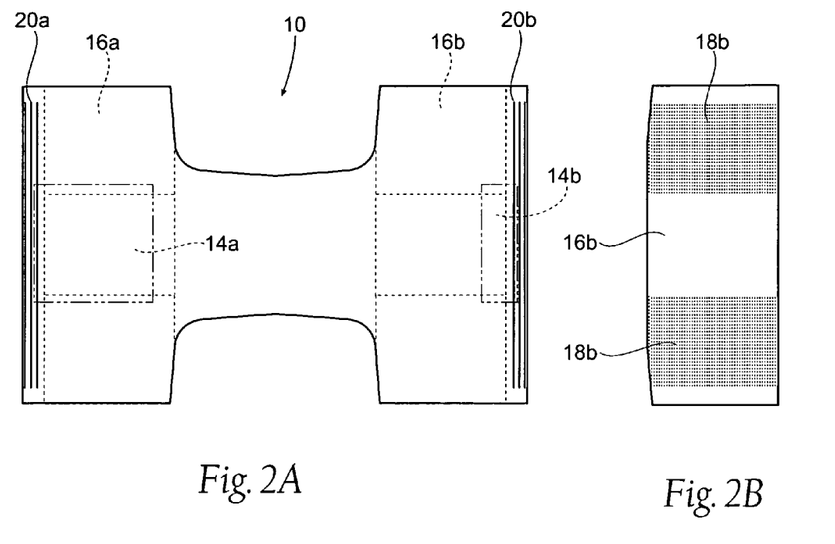

FIG. 2a shows a top view of an undergarment 10 according to the first embodiment of this invention. FIG. 2b shows a side panel 16 of the undergarment 10 of the first embodiment. The stretch elastic film sections 18 are configured such that leg hole elastic is not necessary.

Figure 5:
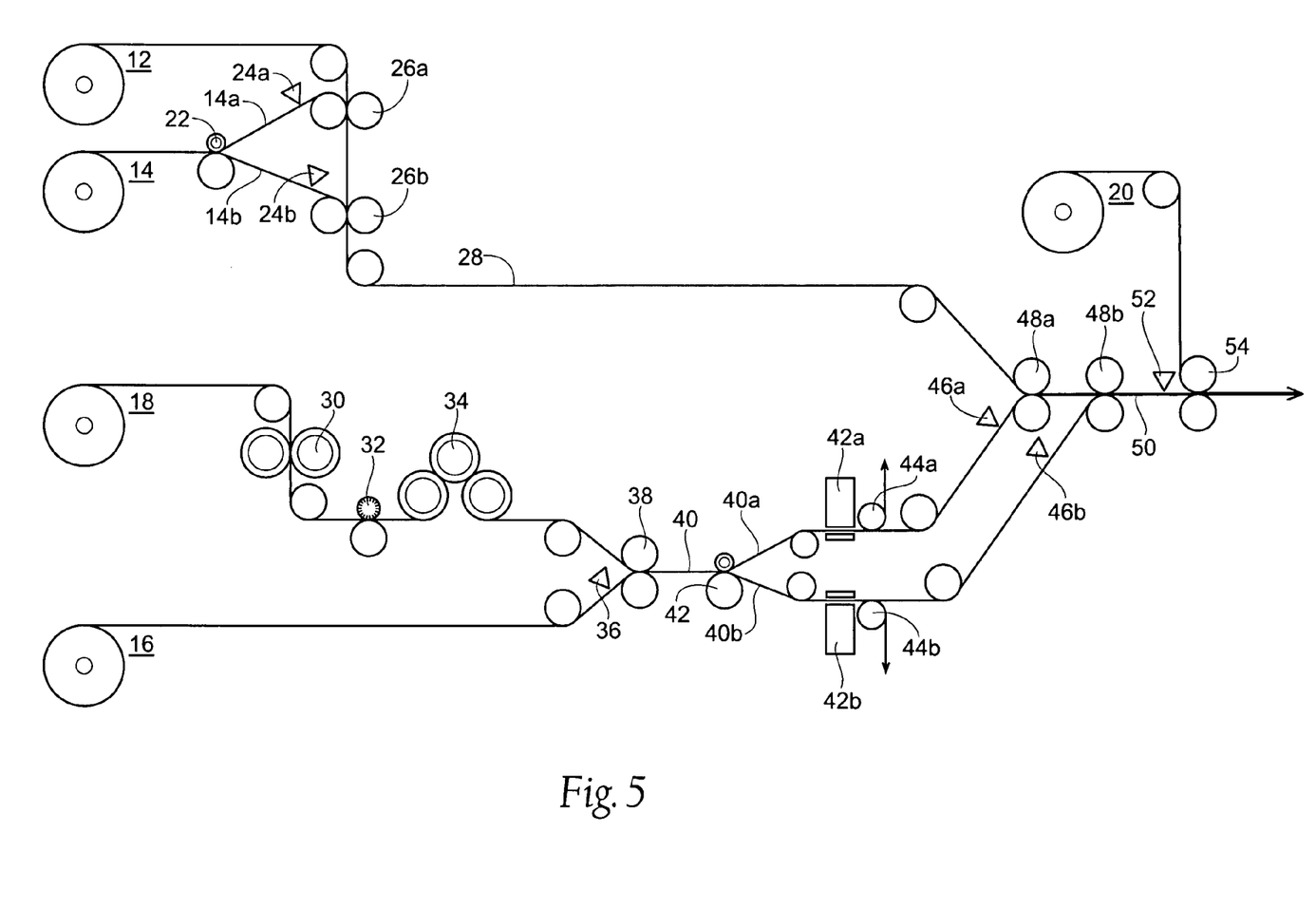
FIG. 5 is a diagrammatic illustration of a method of producing undergarments according to the present invention.

FIG. 5 shows a diagrammatic illustration of an embodiment of the present invention. A system for producing the chassis assembly for disposable undergarments is shown. A roll or layer of chassis nonwoven material 12 is fed into the system. A roll of indicator patch material 14 is unwound and fed through a slitting and spreading station 22 to slit the indicator patch material 14 into two sections and position the separate indicator patch sections 14a and 14b on the process lines. Adhesive applicators 24a and 24b applies adhesive to each of the indicator patch sections 14a and 14b respectively. Each of the separate indicator patch sections 14a and 14b is then applied to the chassis nonwoven material 12 by rollers 26a and 26b respectively. This forms the chassis assembly 28.

At the same time, a roll of elastic film 18 is unwound and fed into the system. A plurality of rollers 30 stretches the elastic film 18 to 300% of its original length and then relaxes the elastic film 18 to 150% of its original length. The elastic film 18 is then perforated for breathability at a perforating station 32. The perforation can be in any pattern; however the preferable pattern is slashes at 45 degrees to the direction of the elastic film 18, for maximum breathability when the elastic film 18 is stretched. The elastic film 18 is then stretched again by a system of chilled rollers 34 to 300% of its original length.

A roll of side panel nonwoven material 16 is fed into the system. An adhesive applicator 36 applies an adhesive coating to the side panel nonwoven material 16. The elastic film 18 is then joined to the side panel nonwoven material 16 by rollers 38 to form the side panel assembly 40. Any suitable adhesive that will sufficiently adhere the elastic film 18 to the side panel nonwoven material 16 may be used; however, a hot melt applicator is preferable. The design of the side panel nonwoven material 16 and the elastic film 18 should determine where and how the adhesive applicator 36 applies and adhesive to the side panel nonwoven layer 16, and any arrangement should not be considered a limiting factor.

Figure 4A:
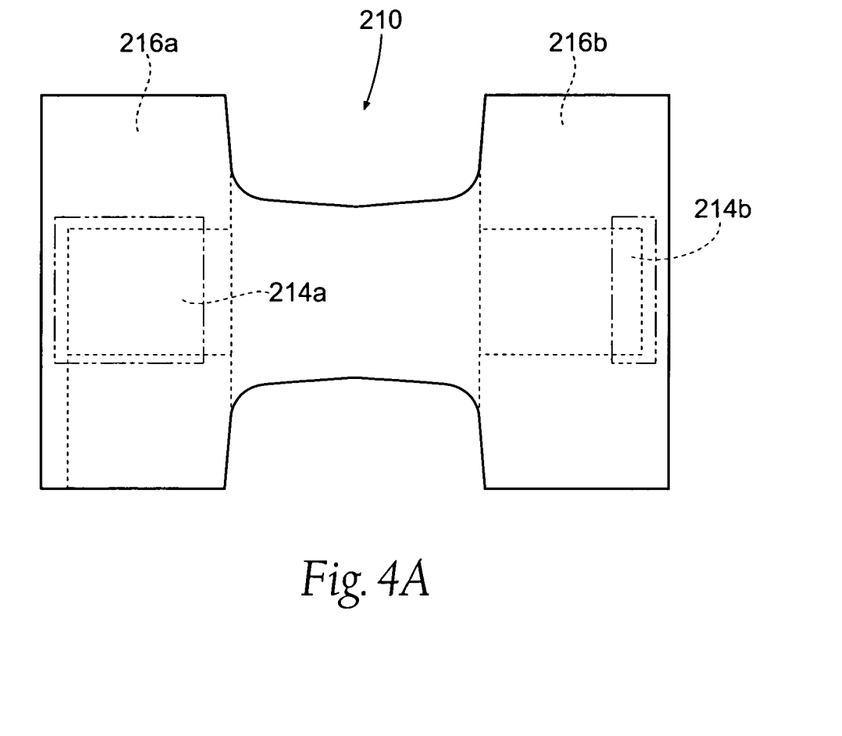
FIG. 4a is a top planar view of an undergarment produced according to the third embodiment of the present invention.

The side panel assembly 40 is then fed through a slitter 42 to form two separate side panel assemblies 40a and 40b. Ultrasonic cutting means 42a and 42b are used to cut only the elastic film 18 in the character patch area 13 in each of the side panel assemblies 40a and 40b. Additionally, a portion of each side panel assembly 40a and 40b near the waistband section of the side panel assembly is cut away. This portion could be cut by any of several cutting means such as a perforated die cuts or ultrasonic cutting means. FIG. 4a shows an undergarment 10 exemplifying a first embodiment of the present invention. FIG. 2b depicts the configuration of one of the side panel assembly 40b after being cut. The side panel assemblies 40a and 40b are mirror images of each other. The adhesive which was selectively applied above is not applied in the character patch area or the waist band area. Vacuum anvils 44a and 44b remove the unwanted elastic film 18 section.

The side panel assemblies 40a and 40b are then adhesively attached to the chassis assembly 28 by adhesive application devices 46a and 46b along with rollers 48a and 48b. The entire undergarment chassis 50 is brought into the main machine for further processing.

An adhesive applicator 52 applies adhesive to the undergarment chassis 50, then waistband elastic 20 is applied by rollers 54. As seen in FIG. 2a waist elastic 20 is applied to opposite sides of the undergarment chassis 50, such that when the undergarment chassis 50 is folded together and the side seams are formed the waist band elastic 20 will entirely encircle the waist area of the undergarment 10.

The undergarment chassis 50 is now further processed according to known means. An adhesive applicator selectively applies an adhesive to the chassis assembly. A succession of absorbent inserts 52 are picked up at a supply station by vacuum heads of a pad supplying/turning device. The absorbent inserts 52 are known in the art and are generally comprised of various absorbent materials contained within a nonwoven material cover. The absorbent inserts 52 are rotated 90 degrees and applied, successively, to the crotch areas of the undergarment chassis by a transfer roll where they are attached adhesively to the inside of the undergarment chassis 50.

Figure 6:
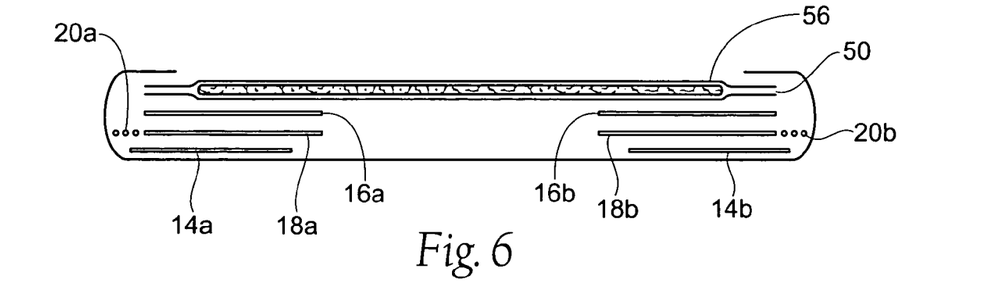
FIG. 6 is a cross-sectional view of an undergarment produced according to the present invention.

An adhesive applicator applies an adhesive to the undergarment chassis. The undergarment chassis 50 is then folded over on its edges to secure the absorbent insert 52. Alternatively, an additional cover nonwoven material strip could be utilized in lieu of folding the undergarment chassis 50 edge over. FIG. 6 is a cross-sectional view of an undergarment 10 produced according to the first embodiment of the present invention including an absorbent insert 52.

The undergarment chassis 50 will proceed for further modifications, such as adding decorative material or cutting of leg holes, if not previously cut, and folding, sealing and severing the web into individual undergarments.

Figures 3A, 3B:
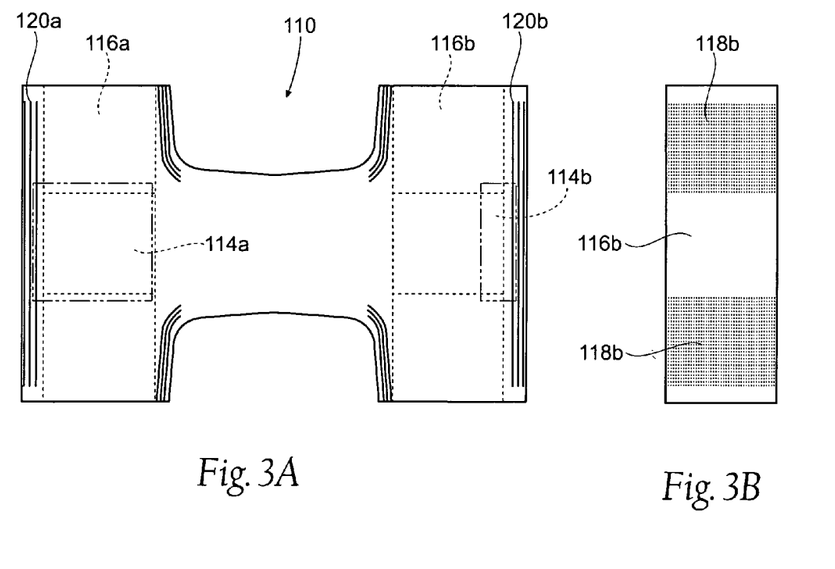

A second embodiment of an undergarment 110 exemplifying the present invention is shown in FIG. 3a. The undergarment 110 of the second embodiment is substantially similar to the undergarment 10 of the first embodiment, however as is seen in FIG. 3b the elastic film 118b is cut in a slightly different configuration. The elastic film 118b is attached to the side panel nonwoven material 116b. The configuration of the elastic film 118a (not shown) attached to the opposite side panel 116a is a mirror image of the elastic film 118b shown in FIG. 3b. In this configuration the elastic film 118a and 118b would not extend to the leg hole of the undergarment 110. This allows the undergarment 110 to be manufactured using leg hole elastic in addition to the elastic film 118a and 118b. In this embodiment the additional step of adhesively applying leg hole elastic is added to the method described above relating to the first embodiment.

Figure 4B:
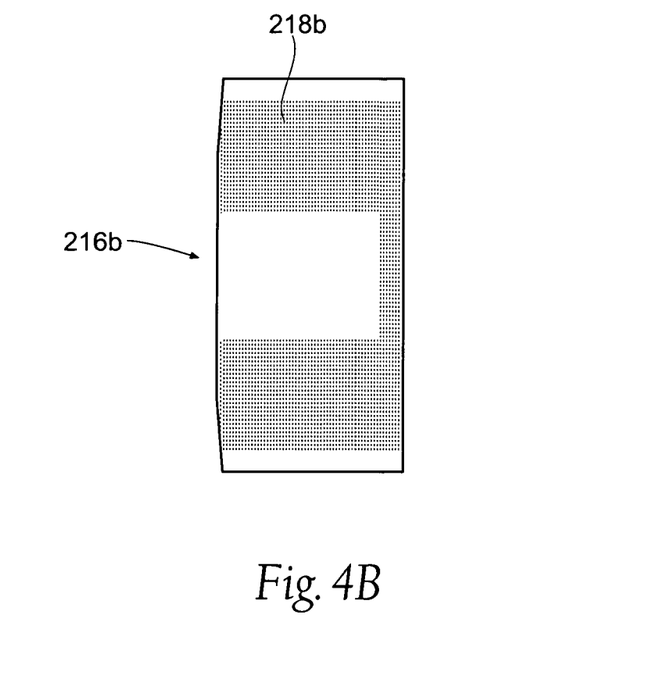

A third embodiment of an undergarment 210 exemplifying the present invention is shown in FIG. 4a. This embodiment of the undergarment 210 does not utilize additional waistband elastic. The shape of the elastic film 218b which is attached to the side is shown in FIG. 4b. The elastic film 218a which is attached to side panel 216a is a mirror image of the elastic film 218b shown in FIG. 4b. As is seen in FIG. 4b, the elastic film 218b is not completely cut through its center. This results in the waistband being elasticized around the entire waist opening when the undergarment 210 is folded and sealed. The undergarment 210 of FIG. 4a is made in substantially the same process as described above referring to the first embodiment. However, the step of applying waistband elastic is omitted. This step can be omitted because the configuration of the elastic film 218a and 218b is different.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method of making a pants type undergarment, the method comprising the steps of:
   a. providing an outer nonwoven layer;
   b. providing a second non-woven layer;
   c. providing a layer of elastomeric material;
   d. stretching said layer of elastomeric material at a first time;
   e. perforating said layer of elastomeric material to form a two-dimensional perforation array of slits on said layer of elastomeric material and stretching said layer of elastomeric material at a second time;
   f. applying intermittent adhesive to said second non-woven layer to create a first and second zone of adhesion, and a zone of non-adhesion;
   g. coupling said stretched and perforated layer of elastomeric material with said second non-woven layer forming a side panel assembly;
   h. slitting said side panel assembly into a front portion and a rear portion;
   i. partially cutting said side panel assembly;
   j. removing said elastomeric material from said side panel assembly in said zone of non-adhesion and coupling said slit and partially cut side panel assembly with said outer non-woven layer in two separate positions on said pants type undergarment, said front portion placed at a first position extending widthwise substantially across a front waist portion of said undergarment, and said rear portion at a second position extending widthwise substantially across a rear waist portion of said undergarment;

said front and rear portions each comprising a first zone of elasticity and a second zone of elasticity, with a third zone of inelasticity formed between said first and second zones.

2. A method according to claim 1, the method further comprising: providing an indicator patch material, slitting and spreading the indicator patch material into at least two sections and positioning the at least two indicator patch sections on said outer nonwoven layer, said indicator patch material provided in positions visible when said pants type undergarment is worn.

3. A method according to claim 1, wherein said two-dimensional perforation array of slits are formed obliquely to a machine direction.

4. A method according to claim 1, the method further comprising:

wherein said two-dimensional perforation array of slits are intermittently formed.

5. A method according to claim 1, the method further comprising:

stretching said perforated layer of elastomeric material a second time prior to applying said intermittent adhesive to said second non-woven layer.

6. The method according to claim 1 further including the steps of:
  a. providing waistband elastic strands; and
  b. adhering said waistband elastic strands to said outer nonwoven layer.

7. The method according to claim 6 further including the steps of:
  a. providing leg elastic strands; and
  b. adhering said leg elastic strands to said outer nonwoven layer.

8. A pants type undergarment constructed according to the method of claim 1.

* * * * *